US00PP17842P3

(12) United States Plant Patent
Hanes

(10) Patent No.: US PP17,842 P3
(45) Date of Patent: Jul. 3, 2007

(54) *VERBENA* PLANT NAMED 'LAN REDTWO'

(50) Latin Name: *Verbena hybrida*
Varietal Denomination: Lan Redtwo

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 222 days.

(21) Appl. No.: 11/094,745

(22) Filed: Mar. 31, 2005

(65) Prior Publication Data

US 2006/0225173 P1 Oct. 5, 2006

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent Bell
*Assistant Examiner*—June Hwu
(74) *Attorney, Agent, or Firm*—Jondle & Associates P.C.

(57) ABSTRACT

A *verbena* cultivar particularly distinguished by red flowers, broad leaves and tolerance to powdery mildew.

1 Drawing Sheet

Figure 1:
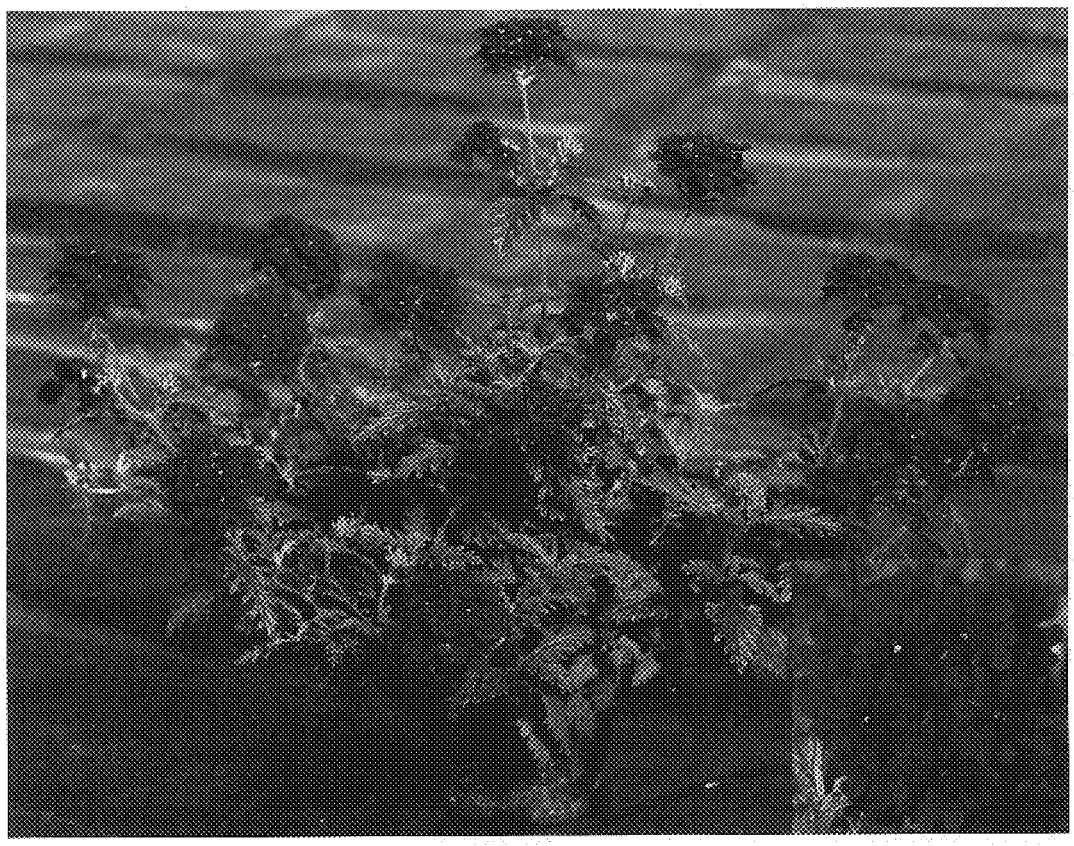

Genus and species: *Verbena hybrida.*
Variety denomination: 'Lan Redtwo'.

BACKGROUND OF THE NEW PLANT

The present invention comprises a new and distinct cultivar of *verbena,* botanically known as *Verbena hybrida,* and hereinafter referred to by the cultivar name 'Lan Redtwo'. The new cultivar originated from a hybridization made in the year 2002 in Gilroy, Calif. The female parent was '1371-1', a red proprietary *verbena* line (unpatented), while the male parent was '1352-1', a purple proprietary *verbena* line (unpatented).

The new cultivar was created in 2002 in Gilroy, Calif. and has been asexually reproduced repeatedly by vegetative cuttings and tissue culture in Gilroy, Calif. and Andijk, The Netherlands over a two-and-a-half-year period. The plant has also been trialed at Gilroy, Calif., Litchfield, Mich. and Andijk, The Netherlands. The present invention has been found to retain its distinctive characteristics through successive asexual propagations.

DESCRIPTION OF PHOTOGRAPH

This new *verbena* plant is illustrated by the accompanying photograph which shows overall plant habit, flowers, and foliage of the plant; the colors shown are as true as can be reasonably obtained by conventional photographic procedures.

FIG. 1. The photograph shows the mature inflorescence.

DESCRIPTION OF THE NEW CULTIVAR

The following detailed descriptions set forth the distinctive characteristics of 'Lan Redtwo'. The data which define these characteristics were collected from asexual reproductions carried out in Gilroy, Calif. The plant history was taken on 5-month-old plants grown in one-gallon pots, in a poly-covered greenhouse. Color readings were taken in the greenhouse in the late winter season under natural light. Color references are primarily to The R.H.S. Colour Chart of The Royal Horticultural Society of London (R.H.S.) (2001 edition). Texture description details were observed under a dissecting microscope.

DETAILED BOTANICAL DESCRIPTION

Classification:
- *Botanical.*—*Verbena hybrida.*
- *Common name.*—*Verbena.*

Growth:
- *Form.*—Compact, low and outwardly spreading, decumbent.
- *Growth and branching habit.*—Vigorous growing, good basal branching.
- *Height.*—18.0–23.0 cm as measured from the top of the soil and excluding any umbels.
- *Width.*—30.0–40.0 cm excluding any umbels.
- *Time to produce a finished flowering plant.*—9 weeks.
- *Outdoor plant performance.*—Does well in full sun, hanging baskets, container plants or garden beds.
- *Time to initiate and develop roots.*—4–10 days.
- *Root description.*—Fibrous, fleshy, white.

Leaves:
- *Immature leaf.*—Color: Upper surface: RHS 137A. Lower surface: RHS 137B. Length: 2.8–3.7 cm. Width: 2.0–2.3 cm.
- *Mature leaf.*—Color: Upper surface: Between RHS 137A and RHS 147A. Lower surface: RHS 137B. Length: 4.3–4.5 cm. Width: 3.0–3.4 cm. Shape: Ovate. Margin: Incised, cleft to parted. Apex: Broadly acute. Base: Attenuate. Texture: Hirsute. Venation: Palmate. Venation color: Between RHS 145B and RHS 145C.
- *Petioles.*—Length: 1.0–1.4 cm. Diameter: 0.2 cm. Color: Between RHS 145B and RHS 145C.

Stems:
- *Color.*—RHS 144A.
- *Length.*—20.0–25.0 cm.

*Diameter.*—0.2 cm.
*Internode length.*—3.0–5.0 cm.
*Texture.*—Hirsute.
*Stem anthocyanin.*—None.

Flower buds:
*Color when bud first showing color.*—RHS 59B.
*Shape.*—Linear.
*Diameter.*—0.2 cm.
*Length.*—1.0–1.2 cm.

Inflorescence:
*Blooming habit.*—Flowers continuously throughout the growing season.
*Lastingness of individual blooms in greenhouse.*—5–7 days.
*Fragrance.*—None.
*Inflorescence type.*—Terminal raceme.
*Racemes.*—Number per plant: 17–35. Diameter: 4.5–5.5 cm. Depth: 2.0–3.0 cm.
*Peduncle.*—Color: RHS 144A. Diameter: 0.1 cm. Length: 4.0–5.5 cm. Texture: Hirsute; few glandular hairs.

Flowers:
*Floret form.*—Salverform; sessile on spikes.
*Floret diameter.*—2.0–2.1 cm.
*Number of petals.*—Gamopetalous, five lobed.
*Immature flower.*—Color: Upper side: Closest to RHS 46B, little deeper at bases of lobes. Underside: RHS 47B, slightly darker at margin, white basally. Diameter: 0.7–0.9 cm.
*Mature flower.*—Color: Upper side: Closest to RHS 46B. Underside: RHS 47B, slightly darker at margin, white basally. Corolla: Color of throat hairs: RHS N155C. Tube length: 1.8–2.0 cm.
*Petals.*—Size: Length of one lobe: 0.9–1.0 cm. Width of one lobe: 0.8–0.9 cm. Lobe shape: Cordate. Apex: Emarginate. Base: Fused. Margin: Entire. Texture: Papillose, velvety.
*Sepals.*—5 sepals, margins are fused to each other along their length, with a transparent membrane of less than 0.1 cm in width, with one smaller sepal (0.7 cm) attached to the base of the calyx.
*Calyx.*—Color: RHS 144A. Length: 1.0 cm. Width: 0.15 cm. Shape: Linear. Apex: Acute.

Reproductive organs:
*Stamens.*—Anthers and filaments fused to upper half of corolla tube; four anthers with two pollen sacs per anther.
*Pollen.*—Amount: Moderate. Color: RHS 10B.
*Pistil.*—1.
*Pistil length.*—1.5 cm.
*Fruit/Seed set.*—Does not freely set seed, but can produce 4 narrow nutlets, approximately 0.4 cm long and enclosed in the dried calyx.

Disease and Insect resistance: Powdery mildew tolerance.

COMPARISON WITH KNOWN CULTIVARS

'Lan Redtwo' differs from the female parent '137-1' (unpatented) by having broader leaves, slightly deeper flower color and greater tolerance to powdery mildew than '1371-1'. 'Lan Redtwo' differs from the male parent '1352-1' (unpatented) by having red flowers, broader leaves and grater powdery mildew tolerance than '1352-1'.

'Lan Redtwo' differs from the commercial variety; Balazreve; also known as 'Aztec Red Velvet' (U.S. Plant Pat. application No. 11/017,174) by having a more upright habit, and leaves that are smaller, more incised and darker than 'Aztec Red Velvet'.

I claim:

1. A new and distinct cultivar of *verbena* plant as shown and described herein.

* * * * *